United States Patent
Roe et al.

(10) Patent No.: US 7,374,546 B2
(45) Date of Patent: *May 20, 2008

(54) INTEGRATED LANCING TEST STRIP

(75) Inventors: Steven N. Roe, San Mateo, CA (US); Charles C. Raney, Camdenton, MO (US); Volker Zimmer, Dossenheim (DE); Jeffrey N. Roe, San Ramon, CA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 691 days.

This patent is subject to a terminal disclaimer.

(21) Appl. No.: 10/767,522

(22) Filed: Jan. 29, 2004

(65) Prior Publication Data

US 2004/0186394 A1    Sep. 23, 2004

Related U.S. Application Data

(60) Provisional application No. 60/443,328, filed on Jan. 29, 2003.

(51) Int. Cl.
*A61B 5/00* (2006.01)

(52) U.S. Cl. ...................................... 600/583
(58) Field of Classification Search ................ 600/583, 600/573, 576, 584; 606/181
See application file for complete search history.

(56) References Cited

U.S. PATENT DOCUMENTS

| | | |
|---|---|---|
| 1,328,459 A | 1/1920 | Smith |
| 2,359,550 A | 10/1944 | Eriksen |
| 2,646,799 A | 7/1953 | Jacoby, Jr. |
| 2,801,633 A | 8/1957 | Ehrlich |
| 3,802,842 A | 4/1974 | Lange et al. |
| D234,644 S | 3/1975 | Sugiyama et al. |
| 4,061,468 A | 12/1977 | Lange et al. |
| 4,095,589 A * | 6/1978 | Manschot et al. .......... 600/584 |
| D254,444 S | 3/1980 | Levine |
| 4,203,446 A | 5/1980 | Hofert et al. |
| 4,360,016 A | 11/1982 | Sarrine |
| 4,375,815 A | 3/1983 | Burns |
| 4,462,405 A | 7/1984 | Ehrlich |

(Continued)

FOREIGN PATENT DOCUMENTS

CA    2287757    4/2001

(Continued)

*Primary Examiner*—Max Hindenburg
*Assistant Examiner*—Emily M. Lloyd
(74) *Attorney, Agent, or Firm*—Woodard, Emhardt, Moriarty, McNett & Henry LLP

(57) ABSTRACT

An integrated bodily fluid sampling device is used to sample a bodily fluid from an incision in skin. The device includes a lancet for forming the incision in the skin. A housing is coupled to the lancet. The housing defines at least in part a capillary channel with an opening. The capillary channel is sized to draw the bodily fluid from the incision via capillary action. A test strip is positioned along the capillary channel for analyzing the fluid. In one form, a flexible sheet extends from the housing proximal the opening of the capillary channel for drawing the bodily fluid into the opening of the capillary channel. In another form, the lancet is slidably received inside the channel. During lancing, the lancet extends from the housing to form the incision. Fluid from the incision is drawn into the channel and is deposited on the test strip for analysis.

48 Claims, 11 Drawing Sheets

U.S. PATENT DOCUMENTS

| | | | |
|---|---|---|---|
| 4,469,110 A | 9/1984 | Slama | |
| 4,490,465 A | 12/1984 | Limbach et al. | |
| 4,627,445 A | 12/1986 | Garcia et al. | |
| 4,637,403 A | 1/1987 | Garcia et al. | |
| 4,653,513 A | 3/1987 | Dombrowski | |
| 4,677,979 A | 7/1987 | Burns | |
| 4,787,398 A | 11/1988 | Garcia et al. | |
| 4,869,249 A | 9/1989 | Crossman et al. | |
| 4,895,147 A | 1/1990 | Bodicky et al. | |
| 4,924,879 A | 5/1990 | O'Brien | |
| 4,990,154 A | 2/1991 | Brown et al. | |
| 5,100,391 A | 3/1992 | Schutte et al. | |
| 5,304,193 A | 4/1994 | Zhadanov | |
| 5,423,847 A | 6/1995 | Strong et al. | |
| 5,529,581 A | 6/1996 | Cusack | |
| 5,540,709 A | 7/1996 | Ramel | |
| 5,545,173 A | 8/1996 | Herbst | |
| 5,582,184 A * | 12/1996 | Erickson et al. | 600/583 |
| 5,607,401 A | 3/1997 | Humphrey | |
| 5,607,437 A | 3/1997 | Simon et al. | |
| 5,613,978 A | 3/1997 | Harding | |
| 5,628,764 A | 5/1997 | Schraga | |
| 5,628,765 A | 5/1997 | Morita | |
| 5,730,753 A | 3/1998 | Morita | |
| RE35,803 E | 5/1998 | Lange et al. | |
| 5,755,733 A | 5/1998 | Morita | |
| 5,776,719 A | 7/1998 | Douglas et al. | |
| 5,798,031 A | 8/1998 | Charlton et al. | |
| 5,824,491 A | 10/1998 | Priest et al. | |
| 5,830,225 A | 11/1998 | Detsch | |
| 5,857,983 A | 1/1999 | Douglas et al. | |
| 5,871,494 A | 2/1999 | Simons et al. | |
| 5,873,887 A | 2/1999 | King et al. | |
| 5,879,311 A | 3/1999 | Duchon et al. | |
| 5,916,230 A | 6/1999 | Brenneman et al. | |
| 5,931,846 A | 8/1999 | Simon et al. | |
| 5,951,492 A | 9/1999 | Douglas et al. | |
| 5,951,493 A | 9/1999 | Douglas et al. | |
| 5,962,215 A | 10/1999 | Douglas et al. | |
| 5,964,718 A | 10/1999 | Duchon et al. | |
| 5,971,941 A | 10/1999 | Simons et al. | |
| 5,984,940 A | 11/1999 | Davis et al. | |
| 5,997,561 A | 12/1999 | Bocker et al. | |
| 6,022,366 A | 2/2000 | Schraga | |
| 6,036,924 A | 3/2000 | Simons et al. | |
| 6,045,497 A * | 4/2000 | Schweich et al. | 600/16 |
| 6,045,567 A | 4/2000 | Taylor et al. | |
| 6,048,352 A | 4/2000 | Douglas et al. | |
| 6,056,701 A | 5/2000 | Duchon et al. | |
| 6,066,103 A | 5/2000 | Duchon et al. | |
| 6,071,250 A | 6/2000 | Douglas et al. | |
| 6,071,294 A | 6/2000 | Simons et al. | |
| 6,086,545 A | 7/2000 | Roe et al. | |
| 6,099,484 A | 8/2000 | Douglas et al. | |
| 6,143,164 A * | 11/2000 | Heller et al. | 600/583 |
| 6,156,050 A | 12/2000 | Davis et al. | |
| 6,156,051 A | 12/2000 | Schraga | |
| 6,159,424 A | 12/2000 | Kauhaniemi et al. | |
| 6,183,489 B1 | 2/2001 | Douglas et al. | |
| 6,210,421 B1 | 4/2001 | Bocker et al. | |
| 6,270,637 B1 | 8/2001 | Crismore et al. | |
| 6,283,982 B1 | 9/2001 | Levaughn et al. | |
| 6,306,152 B1 | 10/2001 | Verdonk et al. | |
| 6,315,738 B1 | 11/2001 | Nishikawa et al. | |
| 6,319,210 B1 | 11/2001 | Douglas et al. | |
| 6,332,871 B1 | 12/2001 | Douglas et al. | |
| 6,346,114 B1 | 2/2002 | Schraga | |
| 6,352,514 B1 | 3/2002 | Douglas et al. | |
| 6,364,890 B1 | 4/2002 | Lum et al. | |
| 6,409,740 B1 | 6/2002 | Kuhr et al. | |
| 6,419,661 B1 | 7/2002 | Kuhr et al. | |
| 6,561,989 B2 | 5/2003 | Whitson | |
| 6,707,554 B1 * | 3/2004 | Miltner et al. | 356/433 |
| 6,800,488 B2 | 10/2004 | Khan | |
| 2001/0027277 A1 * | 10/2001 | Klitmose | 600/583 |
| 2001/0027327 A1 | 10/2001 | Schraga | |
| 2001/0039387 A1 | 11/2001 | Rutynowski et al. | |
| 2002/0002344 A1 | 1/2002 | Douglas et al. | |
| 2002/0004196 A1 | 1/2002 | Whitson | |
| 2002/0016006 A1 | 2/2002 | Wendelbo et al. | |
| 2002/0029059 A1 | 3/2002 | Purcell | |
| 2002/0040230 A1 | 4/2002 | Kuhr et al. | |
| 2002/0082522 A1 | 6/2002 | Douglas et al. | |
| 2002/0103499 A1 | 8/2002 | Perez et al. | |
| 2002/0177761 A1 | 11/2002 | Orloff et al. | |
| 2002/0177763 A1 | 11/2002 | Burns et al. | |
| 2002/0177788 A1 | 11/2002 | Hodges et al. | |
| 2003/0028087 A1 * | 2/2003 | Yuzhakov et al. | 600/345 |

FOREIGN PATENT DOCUMENTS

| | | |
|---|---|---|
| DE | 197 53 847 A1 | 6/1999 |
| EP | 0 582 276 A1 | 2/1994 |
| EP | 1 281 352 A1 | 2/2003 |
| JP | 02000116768 A2 | 4/2000 |
| WO | WO 93/09710 | 5/1993 |
| WO | WO 93/09723 | 5/1993 |
| WO | WO 00/19185 * | 4/2000 |
| WO | WO00/40150 | 7/2000 |
| WO | WO 01/72220 A1 | 10/2001 |
| WO | WO 02/26129 A1 | 4/2002 |
| WO | WO 02/36010 A1 | 5/2002 |
| WO | WO 02/056751 A2 | 7/2002 |
| WO | WO 03/015627 A2 | 2/2003 |

* cited by examiner

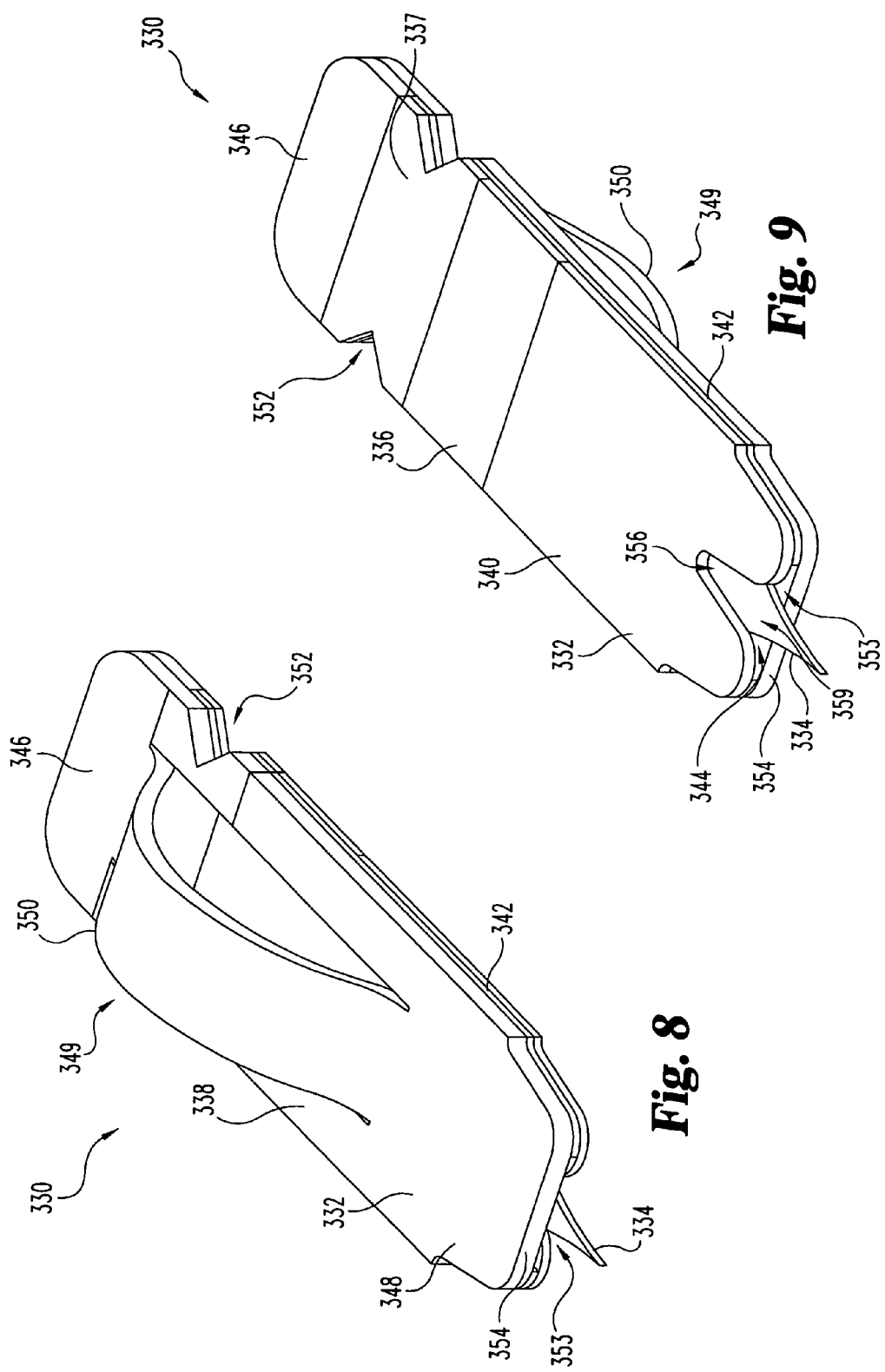

INTEGRATED LANCING TEST STRIP

REFERENCE TO RELATED APPLICATIONS

This application claims the benefit of U.S. Provisional Patent Application Ser. No. 60/443,328 filed Jan. 29, 2003, which is hereby incorporated by reference in its entirety.

BACKGROUND

The present invention generally relates to bodily fluid sampling devices and more specifically, but not exclusively, concerns an integrated lancing test strip.

General Fluid Testing

The acquisition and testing of bodily fluids is useful for many purposes, and continues to grow in importance for use in medical diagnosis and treatment, and in other diverse applications. In the medical field, it is desirable for lay operators to perform tests routinely, quickly and reproducibly outside of a laboratory setting, with rapid results and a readout of the resulting test information. Testing can be performed on various bodily fluids, and for certain applications is particularly related to the testing of blood and/or interstitial fluid. Such fluids can be tested for a variety of characteristics of the fluid, or analytes contained in the fluid, in order to identify a medical condition, determine therapeutic responses, assess the progress of treatment, and the like.

General Test Steps

The testing of bodily fluids basically involves the steps of obtaining the fluid sample, transferring the sample to a test device, conducting a test on the fluid sample, and displaying the results. These steps are generally performed by a plurality of separate instruments or devices.

Acquiring—Vascular

One method of acquiring the fluid sample involves inserting a hollow needle or syringe into a vein or artery in order to withdraw a blood sample. However, such direct vascular blood sampling can have several limitations, including pain, infection, and hematoma and other bleeding complications. In addition, direct vascular blood sampling is not suitable for repeating on a routine basis, can be extremely difficult and is not advised for patients to perform on themselves.

Acquiring—Incising

The other common technique for collecting a bodily fluid sample is to form an incision in the skin to bring the fluid to the skin surface. A lancet, knife or other cutting instrument is used to form the incision in the skin. The resulting blood or interstitial fluid specimen is then collected in a small tube or other container, or is placed directly in contact with a test strip. The fingertip is frequently used as the fluid source because it is highly vascularized and therefore produces a good quantity of blood. However, the fingertip also has a large concentration of nerve endings, and lancing the fingertip can therefore be painful. Alternate sampling sites, such as the palm of the hand, forearm, earlobe and the like, may be useful for sampling, and are less painful. However, they also produce lesser amounts of blood. These alternate sites therefore are generally appropriate for use only for test systems requiring relatively small amounts of fluid, or if steps are taken to facilitate the expression of the bodily fluid from the incision site.

Various methods and systems for incising the skin are known in the art. Exemplary lancing devices are shown, for example, in U.S. Pat. No. Re. 35,803, issued to Lange, et al. on May 19, 1998.; U.S. Pat. No. 4,924,879, issued to O'Brien on May 15, 1990; U.S. Pat. No. 5,879,311, issued to Duchon et al. on Feb. 16, 1999; U.S. Pat. No. 5,857,983, issued to Douglas on Jan. 12, 1999; U.S. Pat. No. 6,183,489, issued to Douglas et al. on Feb. 6, 2001; U.S. Pat. No. 6,332,871, issued to Douglas et al. on Dec. 25, 2001; and U.S. Pat. No. 5,964,718, issued to Duchon et al. on Oct. 12, 1999. A representative commercial lancing device is the Accu-Chek Softclix lancet.

Expressing

Patients are frequently advised to urge fluid to the incision site, such as by applying pressure to the area surrounding the incision to milk or pump the fluid from the incision. Mechanical devices are also known to facilitate the expression of bodily fluid from an incision. Such devices are shown, for example, in U.S. Pat. No. 5,879,311, issued to Duchon et al. on Feb. 16, 1999; U.S. Pat. No. 5,857,983, issued to Douglas on Jan. 12, 1999; U.S. Pat. No. 6,183,489, issued to Douglas et al. on Feb. 6, 2001; U.S. Pat. No. 5,951,492, issued to Douglas et al. on Sep. 14, 1999; U.S. Pat. No. 5,951,493, issued to Douglas et al. on Sep. 14, 1999; U.S. Pat. No. 5,964,718, issued to Duchon et al. on Oct. 12, 1999; and U.S. Pat. No. 6,086,545, issued to Roe et al. on Jul. 11, 2000. A representative commercial product that promotes the expression of bodily fluid from an incision is the Amira AtLast blood glucose system.

Sampling

The acquisition of the produced bodily fluid, hereafter referred to as the "sampling" of the fluid, can take various forms. Once the fluid specimen comes to the skin surface at the incision, a sampling device is placed into contact with the fluid. Such devices may include, for example, systems in which a tube or test strip is either located adjacent the incision site prior to forming the incision, or is moved to the incision site shortly after the incision has been formed. A sampling tube may acquire the fluid by suction or by capillary action. Such sampling systems may include, for example, the systems shown in U.S. Pat. No. 6,048,352, issued to Douglas et al. on Apr. 11, 2000; U.S. Pat. No. 6,099,484, issued to Douglas et al. on Aug. 8, 2000; and U.S. Pat. No. 6,332,871, issued to Douglas et al. on Dec. 25, 2001. Examples of commercial sampling devices include the Roche Compact, Amira AtLast, Glucometer Elite and Therasense FreeStyle test strips.

Testing General

The bodily fluid sample may be analyzed for a variety of properties or components, as is well known in the art. For example, such analysis may be directed to hematocrit, blood glucose, coagulation, lead, iron, etc. Testing systems include such means as optical (e.g., reflectance, absorption, fluorescence, Raman, etc.), electrochemical, and magnetic means for analyzing the sampled fluid. Examples of such test systems include those in U.S. Pat. No. 5,824,491, issued to Priest et al. on Oct. 20, 1998; U.S. Pat. No. 5,962,215, issued to Douglas et al. on Oct. 5, 1999; and U.S. Pat. No. 5,776,719, issued to Douglas et al. on Jul. 7, 1998.

Typically, a test system takes advantage of a reaction between the bodily fluid to be tested and a reagent present in the test system. For example, an optical test strip will generally rely upon a color change, i.e., a change in the wavelength absorbed or reflected by dye formed by the reagent system used. See, e.g., U.S. Pat. Nos. 3,802,842; 4,061,468; and 4,490,465.

Blood Glucose

A common medical test is the measurement of blood glucose level. The glucose level can be determined directly by analysis of the blood, or indirectly by analysis of other fluids such as interstitial fluid. Diabetics are generally instructed to measure their blood glucose level several times a day, depending on the nature and severity of their diabetes. Based upon the observed pattern in the measured glucose levels, the patient and physician determine the appropriate level of insulin to be administered, also taking into account such issues as diet, exercise and other factors.

In testing for the presence of an analyte such as glucose in a bodily fluid, test systems are commonly used which take advantage of an oxidation/reduction reaction which occurs using an oxidase/peroxidase detection chemistry. The test reagent is exposed to a sample of the bodily fluid for a suitable period of time, and there is a color change if the analyte (glucose) is present. Typically, the intensity of this change is proportional to the concentration of analyte in the sample. The color of the reagent is then compared to a known standard which enables one to determine the amount of analyte present in the sample. This determination can be made, for example, by a visual check or by an instrument, such as a reflectance spectrophotometer at a selected wavelength, or a blood glucose meter. Electrochemical and other systems are also well known for testing bodily fluids for properties on constituents.

Testing Difficulties

Performing the above-discussed steps can be difficult for patients, especially for patients with limited hand dexterity, such as the elderly. In a typical procedure, the patient first creates an incision in the skin by lancing the skin with a lancet. When the incision is being formed, the skin can tend to deform or bulge such that the lancet forms an incision with a greater depth than needed. As one should appreciate, the greater penetration depth of the lancet into the skin results in more pain associated with lancing for the user. Once a sufficient amount of fluid collects as droplet on the skin, the patient has to position a test strip over the site such that the test strip contacts and absorbs a sufficient amount of the droplet for testing. In another collection technique, the user positions a capillary tube over the incision site and transfers the fluid from the incision onto a test strip with the capillary tube. Usually the droplets of fluid are quite small, and patients, especially ones with hand motor control problems, may experience great difficulty in positioning the test strip or capillary tube so as to collect a sample from the droplet. Moreover, the incision may be closed when excessive pressure is applied to the skin by the test strip or capillary tube, thereby reducing the fluid supply from the incision. As should be appreciated, patients can become frustrated by this procedure, and consequently, they may perform the test less often or may even quit testing altogether.

Thus, needs remain for further contributions in this area of technology.

SUMMARY

One form of the present invention generally concerns a device for sampling bodily fluid from an incision in the skin. The device includes a lancet for forming the incision in the skin and a housing coupled to the lancet. The housing defines at least in part a capillary channel with an opening. The capillary channel is sized to draw the bodily fluid from the incision via capillary action. A flexible sheet extends from the housing proximal the opening of the capillary channel to draw the bodily fluid into the opening of the capillary channel.

A further form concerns a method for sampling bodily fluid from an incision in the skin. A device is provided that includes a housing that defines a capillary channel with an opening. A lancet is coupled to the housing, and a flexible sheet extends from the housing proximal the opening of the capillary channel. The incision in the skin is lanced with the lancet. The bodily fluid is drawn from the incision into the capillary channel with the sheet.

Another form concerns an integrated bodily fluid sampling device for sampling bodily fluid from an incision in the skin. The device includes a housing that defines a capillary channel with an opening, and a flat lancet that is slidably received in the channel. The lancet has a lancet tip configured to form the incision in the skin. The lancet tip has a first position at which the lancet tip is positioned inside the housing and a second position at which the lancet tip extends from the opening of the channel to form the incision in the skin. The device further includes means for testing the bodily fluid positioned along the channel. The capillary channel is sized to draw via capillary action the bodily fluid from the incision onto the means for testing the bodily fluid.

Still yet another form concerns an integrated bodily fluid sampling device for sampling a bodily fluid from an incision in the skin. The device includes a housing that defines a capillary channel with an opening configured to draw the bodily fluid via capillary action. A lancet has a lancet tip for forming the incision in the skin, and the lancet is attached to the housing with the lancet tip extending from around the opening of the channel. The lancet is immovable with respect to the housing. Means for testing the bodily fluid is positioned along the channel.

Further forms, objects, features, aspects, benefits, advantages, and embodiments of the present invention will become apparent from a detailed description and drawings provided herewith.

BRIEF DESCRIPTION OF THE DRAWINGS

FIG. 8 is a top perspective view of an integrated lancing test strip according to a further embodiment of the present invention.

FIG. 9 is a bottom, perspective view of the FIG. 8 lancet.

DESCRIPTION OF THE SELECTED EMBODIMENTS

Figure 1:
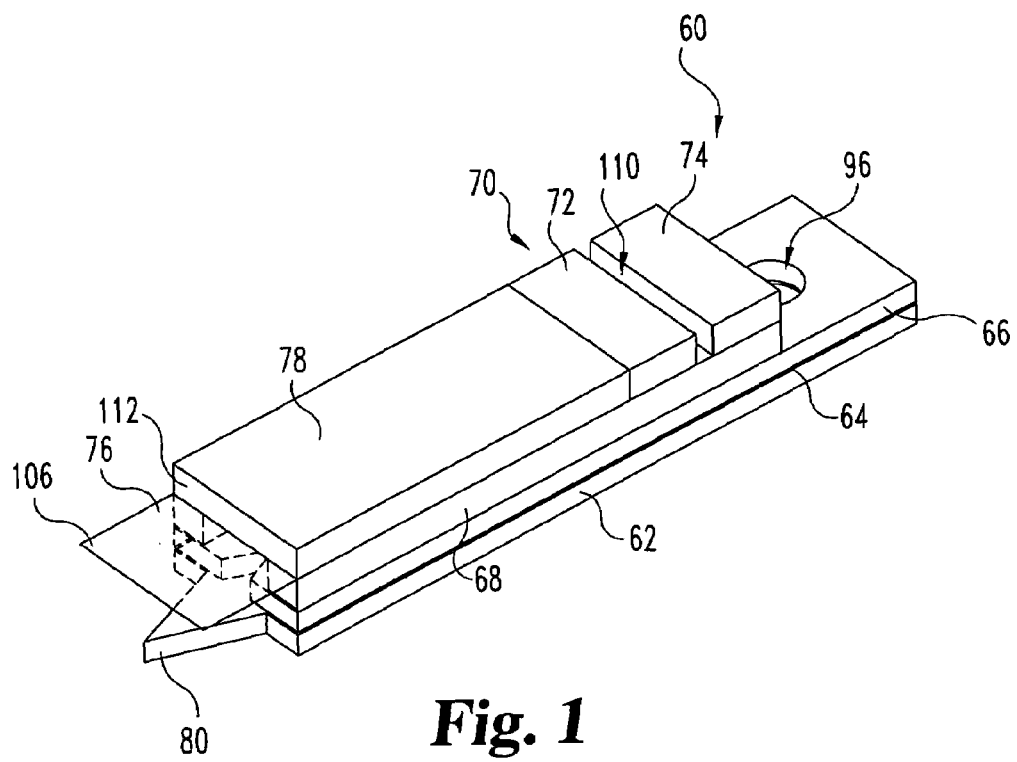
FIG. 1 is a perspective view of an integrated test strip according to one embodiment of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention generally concerns an integrated skin lancing device that reduces the number of steps involved in collecting and analyzing bodily fluid samples. The device includes a lancet for forming an incision in the skin as well as a housing that defines a capillary channel for drawing fluid from the incision onto a test strip located in the housing. In one form, the device has an overall flat shape such that manufacturing of the device is simplified so that its components can be laminated together to form the device. With the integrated design, the user does not have to reposition or reorient a capillary tube or a test strip over the incision in order to draw and analyze a sample.

In one embodiment, one or more spacer members are sandwiched between a base member and a sheet of flexible, hydrophilic film so as to define the capillary channel with an opening. The lancet is attached to the base and has a tip for lancing that extends past the opening of the capillary channel. In one particular form, the hydrophilic film extends past the opening of the capillary channel so as to promote wicking of the bodily fluid sample into the channel. Due to its flexible nature, the hydrophilic film bends against the skin during lancing. After the skin is lanced, the hydrophilic film remains in contact with the skin, and the fluid is drawn via capillary action between the hydrophilic film and the lancet's tip. Since the hydrophilic film is flexible, the film does not significantly deform the skin such that the incision in the skin remains open during collection of the fluid sample. If the hydrophilic film were rigid, however, the skin would tend to deform such that the incision would prematurely close, thereby cutting off the fluid supply. Moreover, one of the many benefits of having the lancet already positioned proximal the opening of the capillary channel is that the opening of the channel does not have to be repositioned over the incision after lancing. The integrated lancing device further includes a testing means positioned along the capillary channel for analyzing the bodily fluid sample. In one form, the testing means includes a chemical reagent test strip. The testing means in another form includes two or more electrodes that are operatively coupled to an electrochemical reagent test strip.

In a further embodiment, the lancet is slidably received inside the capillary channel. The lancet in this embodiment is generally flat. By being positioned inside the channel, the lancet is supported and stabilized by the housing throughout the entire lancing stroke so that the lancet remains in proper alignment during lancing. The support provided by the housing around the lancet prevents the lancet from laterally deflecting or bending during lancing, which in turn prevents the incision from being formed at the wrong location or angle. As will be appreciated from the discussion below, this design also allows the flat lancet to be formed from thinner material than previously possible, which in turn may reduce the pain associated with lancing. Moreover, this configuration ensures that the capillary channel is positioned directly over the incision. The device further includes a retraction mechanism for retracting the lancet into the housing after lancing the skin. During lancing, the lancet extends from the opening of the capillary channel so as to form an incision in the skin. In one form, the device has a skin contacting edge positioned next to the opening of the capillary channel in order to provide a reference surface for flattening the skin around the lancet. By flattening the skin around the lancet, an incision with a precise depth can be formed. In a further form, the device incorporates an adjustment mechanism for adjusting the penetration depth of the lancet. Once the skin has been lanced, the retraction mechanism withdraws the lancet back into the housing. The bodily fluid from the incision is then drawn into the channel and around the lancet via capillary action. As should be appreciated, by having the lancet positioned within the capillary channel, the opening of the capillary channel is positioned over the incision site before lancing. This eliminates the need to reposition the capillary over the incision subsequent to lancing the incision. After the fluid has been drawn within the capillary channel, the fluid is then transported to a means for testing the fluid, such as a test strip.

As will be appreciated from the discussion below, the number of steps involved in obtaining a sample is significantly reduced using the integrated device according to the present invention. The capillary channel in the integrated device does not have to be repositioned over the incision after lancing. Consequently, the difficulties associated with moving a capillary tube quickly and accurately to the incision site are significantly reduced. It therefore enhances the ability to acquire the expressed body fluid without loss, delay or contamination. Moreover, the devices according to the present invention are useful for sampling and analyzing various type bodily fluids. For example, the devices can be suitable for sampling either blood or interstitial fluid.

Figure 2:
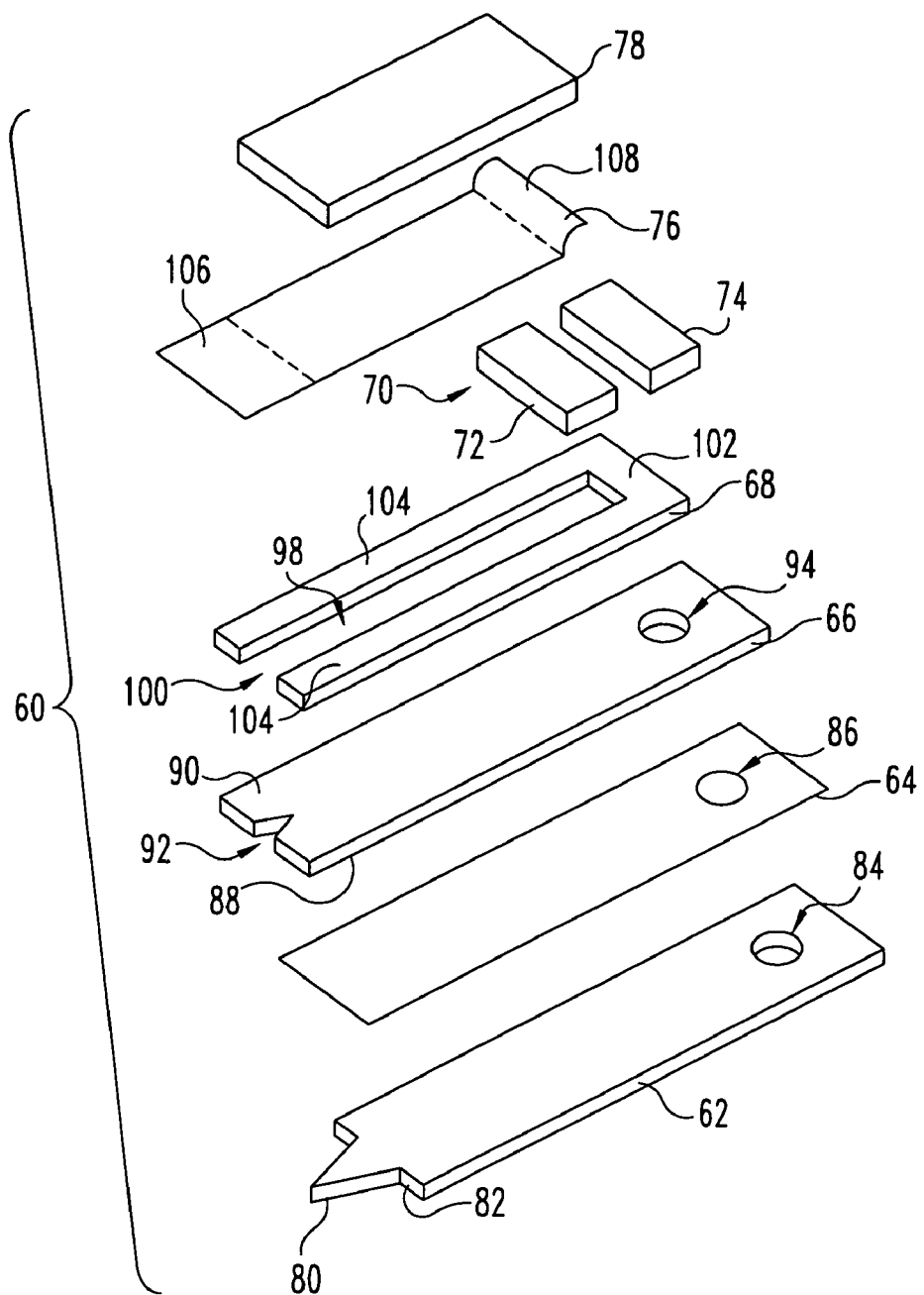
FIG. 2 is an exploded view of the FIG. 1 test strip.

An integrated sampling device 60, according to one embodiment of the present invention, will now be described with reference to FIGS. 1-3. As illustrated in FIGS. 1 and 2, device 60 includes an incision forming member or lancet 62, a layer of adhesive or adhesive tape 64, a base 66, a spacer 68, a testing area 70 that includes a test strip 72, a vent member 74, and a collection sheet or member 76 for drawing a fluid sample into the device 60. Device 60 can be used to manually or automatically lance an incision in the skin and analyze the fluid drawn from the incision. During lancing, the lancet 62 cuts an incision in the skin such that a droplet of bodily fluid is formed on the skin. The collection sheet 76 is then used to wick the bodily fluid into a capillary cavity that is defined by the spacer 68, and the fluid is then deposited on the test strip 72 for analysis. For the sake of clarity and brevity, other components of device 60 that are well know in the art, such has hammers, cocking mechanisms and the like that are not important to appreciate the present invention, will not be discussed below. For examples of such components, please refer to U.S. Patent No. 5,964,718, issued to Duchon et al. on Oct. 12, 1999, which is hereby incorporated by reference in its entirety. In the illustrated embodiment, the lancet 62 has a generally flat shape such that device 60 has an overall flat shape. By being substantially flat, the lancet 62 as well as the other components can be easily formed from sheets of material, such as metal or plastic, and these sheets can be sandwiched together in order to mass produce sampling devices 60. Moreover, the flat design allows multiple sampling devices 60 to be connected together for use in a cartridge, such as the drum in an ACCU-CHEK® ADVANTAGE® brand meter (Roche Diagnostics Corporation, Indianapolis, Ind.). The sampling device 60 can also be a stand-alone lancet that is dispensed and used individually.

Figure 1A:
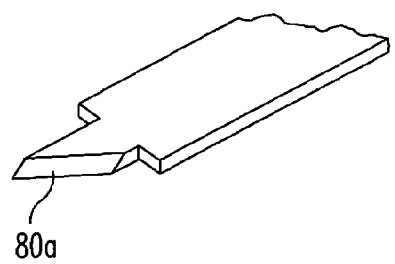
FIG. 1a is a perspective view of a lancet tip according to another embodiment of the present invention.

In one embodiment, the lancet 62 is made of metal, in particular stainless steel, but it is contemplated that the lancet 62 can be made of other materials, such as plastic and/or ceramics. As shown in FIG. 2, the lancet 62 has a lancet tip or blade 80 extending from a stop edge 82 at one end of the lancet 62. The lancet tip 80 in the illustrated embodiment is sharp such that it is able to cut an incision into the skin, and the stop edge 82 limits the penetration depth of the lancet tip 80 into the skin. In the illustrated embodiment, the lancet tip 80 has a generally triangular cross sectional shape. However, it is contemplated that the lancet tip 80 can be shaped differently. For example, FIG. 1a shows a lancet tip 80a with a slanted shape. Near the end opposite the stop edge 82, the lancet 62 defines a registration opening 84 that is used to secure and position the device 60 within a bodily fluid testing meter. Layer 64 is used to secure the lancet 62 to the base 66. As shown, layer 64 defines a registration opening 86 that is positioned to align with the registration opening 84 in the lancet 62. In one embodiment, layer 64 is a layer of adhesive, and in another embodiment, layer 64 is a piece of double-sided adhesive tape. As should be appreciated, layer 64 can include other types of means for securing components together, such as a weld or the like. To prevent infection, the lancet 62 typically is sterilized. However, the sterilization process can affect the test strip 72 such that the test strip 72 has to be recalibrated after sterilization. With the construction of device 60, the lancet 62 or the test strip 72 can be secured to the device 60 after sterilization so as to avoid the undesirable affects of sterilization on the test strip 72.

With continued reference to FIG. 2, the base 66 has a lancet engaging surface 88 to which the lancet 62 is secured and an opposite spacer engaging surface 90 to which spacer 68 is secured. The lancet engaging surface 88 is coated with the adhesive layer 64 such that the lancet 62 is secured to the base 66. In one embodiment, the spacer 68 is attached to the base 66 with an adhesive or adhesive tape, but it is contemplated that the spacer 68 can be secured in other manners. In other embodiments, the base 66 can be optional such that the spacer 68 is directly attached to the lancet 62. At the end proximal the lancet tip 80, the base 66 defines a notch 92 that is used to reduce the phenomenon called "dose hesitation". When a sample is collected, the sample can tend to hesitate in its introduction into the capillary. This dose hesitation increases the time required in order to collect an adequate sample. With notch 92, the dose hesitation effect is substantially reduced. The notch 92 in the illustrated has a v-shape. Like lancet 62, base 66 defines a registration opening 94 that is positioned and sized to align with opening 84 in the lancet 62. Together, openings 84, 86 and 94 form a registration opening 96 in device 60, as shown in FIG. 1. Registration opening 96 is used to position and secure device 60 in a meter.

In FIG. 2, the spacer member 68 defines a capillary channel or cavity 98 through which fluid is collected. In one embodiment, the spacer 68 is made from a piece of adhesive tape. It should be understood that the spacer 68 can be formed from other materials, such as a bead of adhesive and/or a piece of plastic, to name a few. At the one end near the lancing tip 80, the channel 98 has a capillary opening 100 in which the bodily fluid sample is received. At the end of channel 98, opposite opening 100, an end portion 102 encloses channel 98. In the illustrated embodiment, the channel 98 is defined by end portion 102 and a pair of arms 104 that extend from portion 102 along the base 66. The spacer 68, as well as channel 98, is sandwiched between base 66 and collection member 76. Once enclosed, channel 98 is dimensioned so as to draw the bodily fluid sample into the device 60 via capillary action. For instance, the spacer 68 in one embodiment spaces the base 66 and collection sheet 76 apart from one another between two-thousandths of an inch (0.002") and ten-thousandths of an inch (0.010") to form the capillary channel 98 of that size. In another form, base 66 and sheet 76 are preferably spaced apart between about two-thousandths of an inch (0.002") to three-thousandths of an inch (0.002") so as to improve the flow rate in the capillary channel 98.

As briefly mentioned above, the collection member 76 is used to draw the fluid sample into the capillary channel 98 via opening 100. In the illustrated embodiment, collection member 76 is in the form of a flexible sheet. By being flexible, the sheet 76 is able to deform during lancing, and yet is able to contact the skin without closing the incision in order to wick the fluid from the incision into the device 60. In one particular form, sheet 76 is a transparent plastic film so as to allow the user to visualize the incision and the droplet of fluid during sampling. Moreover, sheet 76 provides a visual indicator such that the user can see whether the device 60 is positioned close enough to collect the fluid. As should be appreciated, in other embodiment, the sheet 76 can be semi-transparent and/or opaque. Sheet 76 has a sampling end portion 106 that is configured to contact the skin during sampling. The sampling end portion 106 flexes during collection of fluid so that only a minimal amount of force is applied to the skin such that fluid flow from the incision is not restricted. Sheet 76 further includes a collection end portion 108 that is received between support 78 and test area 70. Collection end portion 108 isolates the test area 70 from the support 78 so as to enhance fluid flow onto the test strip 72. In one embodiment, the flow of fluid may be enhanced by forming the base 66, the spacer 68 and/or the sheet 76 along channel 98 from a material which is hydrophilic, which has been treated to be hydrophilic, or which has been coated with a hydrophilic material such as a surfactant or hydrophilic polymers. The surfaces can also be treated using polyamides, oxidation (e.g. corona/plasma treatment); plasma chemical vapor deposition; vacuum vapor deposition of metals, metaloxides or non-metaloxides; or deposition of an element which oxidizes with water. In one specific form, the entire sheet 76 is coated with a layer of aluminum oxide in order to enhance wicking of fluid into the device 60.

The test strip 72 is positioned along capillary channel 98 so that test strip 72 is able to collect fluid drawn into the capillary channel 98. The test strip 72 can analyze fluid through such means as optical (e.g., reflectance, absorption, fluorescence, RAMAN, etc.), electrochemical and/or magnetic analysis, to name a few. In one embodiment, test strip 72 is a chemically reactive reagent test strip. It should be appreciated that test strip 72 can analyze fluid in other manners. Optionally, an absorbent pad may be placed between the test strip in the closed end of the capillary channel 98 for wicking body fluid onto the test strip 72. In one embodiment where the test strip 72 is disposed within the capillary channel 98, no absorbent pad may be needed because the test strip will be in direct contact with the body fluid. As shown in FIG. 1, the vent member 74 is attached to end portion 102 of the spacer 68 such that a vent opening 110 for channel 98 is defined between the test strip 72 and the vent member 74. The vent opening 110 is used to exhaust air or some other gas from the capillary channel 98, thereby improving the fluid flow in the channel 98. Support 78 is attached to sheet 76 so as to act is a support backing for the sheet 76. In one embodiment, the support 78 is attached to the sheet 76 through an adhesive, and test strip 72 as well as vent member 74 are likewise attached to the spacer 68 through an adhesive. It should be appreciated, however, that these components can be attached to device 60 in other generally known manners.

As mentioned above, the overall, flat design of device 60 aids in improving the manufacturability of the device 60. Referring to FIG. 1, once the components of device 60 are assembled, they form a sampling end at opening 100 from which the lancet tip 80 and sampling end portion 106 of sheet 76 extend. As shown, the sheet 76 and the lancet tip 80 extend in a generally parallel relationship. However, it should be appreciated that due to the flexibility of sheet 76, sheet 76 may deflect towards or away from tip 80, depending on the orientation of device 60. As shown in FIG. 3, a gap 114 is formed between sheet 76 and lancet tip 80 for drawing fluid via capillary action. In one embodiment, sampling portion 106 of the sheet 76 has the same length as tip 80. In another embodiment, sampling end portion 106 of sheet 76 extends past tip 80 such that sheet 76 can remain in contact with the skin after the lancet tip 80 has been withdrawn from the skin. It is further contemplated that the sampling end portion 106 can be shorter than tip 80 when device 60 is oriented to lance a curved surface (such as a fingertip) or at an angle where sheet 76 can still contact the skin when the lancet tip 80 is removed from the skin.

Figure 3:
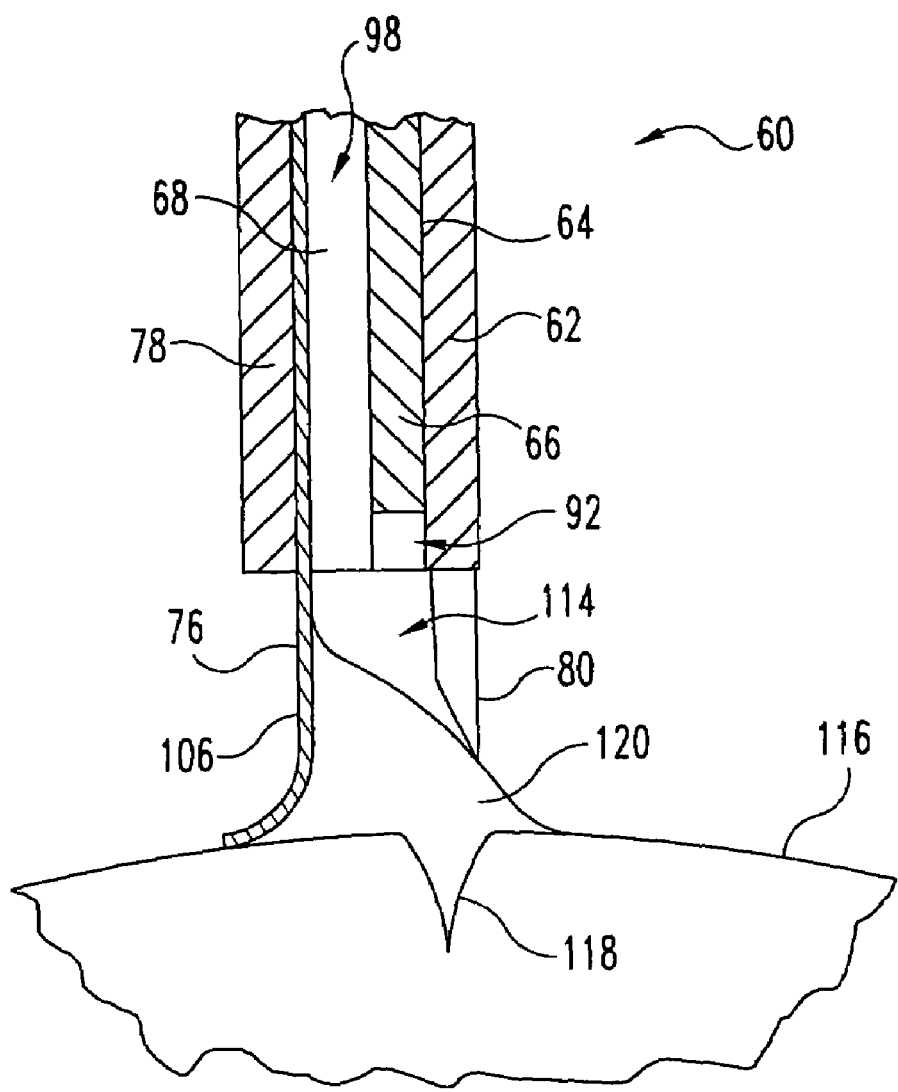
FIG. 3 is a cross sectional view of the FIG. 1 lancet during sampling of bodily fluids.

With reference to FIG. 3, during lancing, sheet 76 contacts and bends against skin 116 as the lancet tip 80 is driven towards the skin 116. After incision 118 is formed in the skin 116 by the lancet tip 80, the lancet tip 80 is retracted from the incision 118 so as to allow bodily fluid 120 to flow from the incision 118. The lancet 62 can be retracted from the incision 118 either manually by the user, or automatically through a retraction mechanism, such as a spring. After lancing, the device 60 is positioned proximal to the skin 116 in order to collect fluid 120 from the incision 118. One of the many benefits of device 60 is that positioning of the device 60 for collecting fluid 120 is simplified. The device 60 does not have to be reoriented or repositioned after lancing in order to collect the fluid 120. Moreover, sheet 76 provides a visual indicator to the user so as to ensure that the device 60 is positioned at the appropriate distance from the skin 116 for drawing fluid 120 from incision 118. In the illustrated embodiment, the sampling end portion 106 of sheet 76 contacts the skin 116 during fluid collection. As mentioned above, if excessive force is applied to the skin 116 through a rigid member, such as the lancet tip 80 for example, the skin 116 tends to deform or dimple, which in turn closes the incision 118. By prematurely closing the incision 118, the amount of fluid 120 collected on the skin 116 during sampling is significantly reduced. Due to its flexible nature, sheet 76 does not substantially compress skin 116 such that the fluid flow from the incision 118 is not restricted. In another embodiment, the sheet 76 is positioned slightly away from the skin 116 so as to not touch the skin 116, but is still positioned close enough to draw the fluid 120 from the droplet of fluid 120. As mentioned above, sheet 76 can be optionally coated or made from a hydrophilic material for enhancing fluid flow along sheet 76 and into the capillary channel 98. From gap 114, the fluid 120 is drawn via capillary action into channel 98, and the fluid 120 from channel 98 is then deposited on the test strip 72 in test area 70. The fluid 120 can then be analyzed with the test strip 72 in order to determine the desired feature, such as selected analyte levels in the fluid 120.

Figure 4:
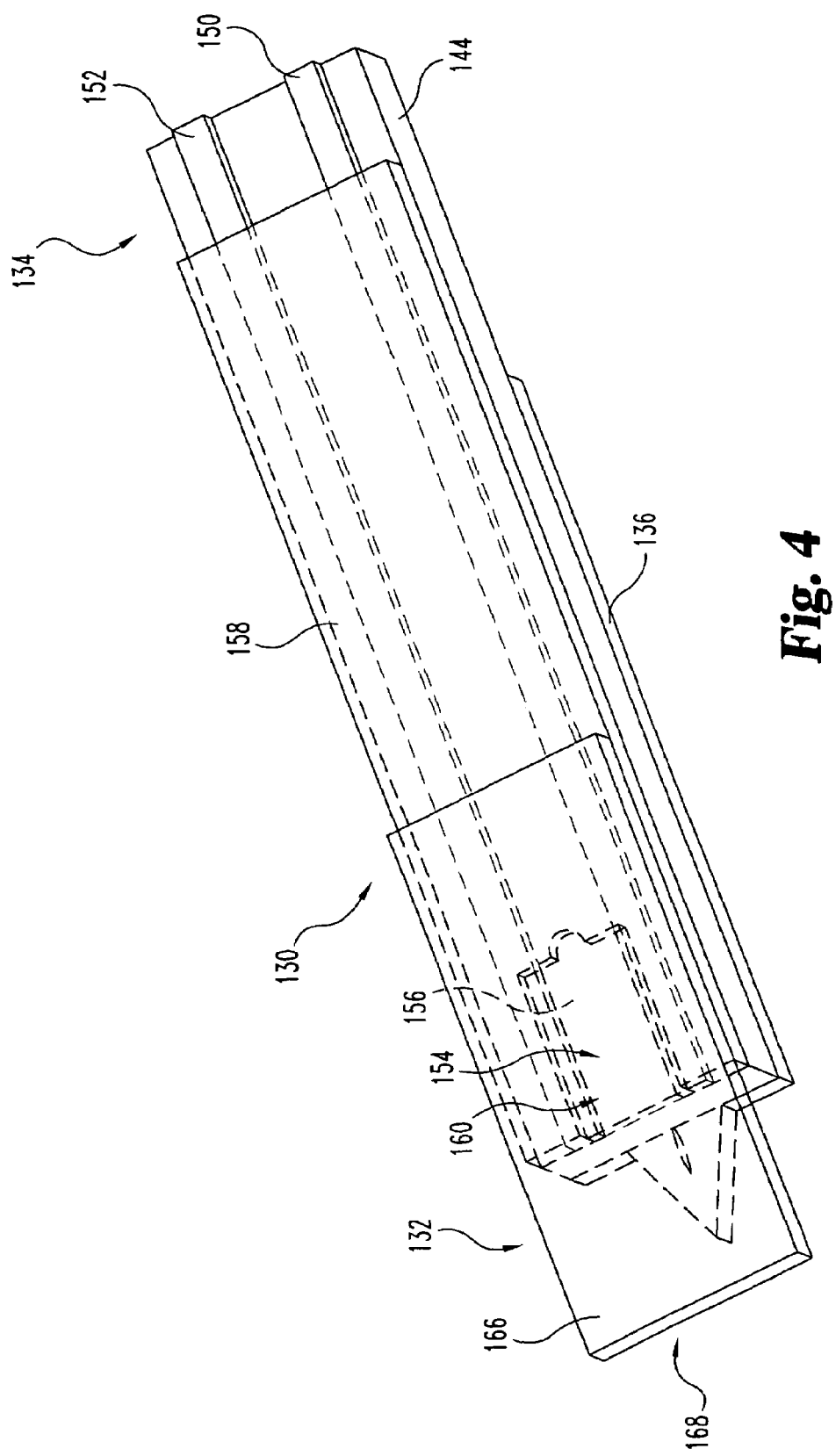
FIG. 4 is a perspective view of an integrated lancing strip according to another embodiment of the present invention.
Figure 5:
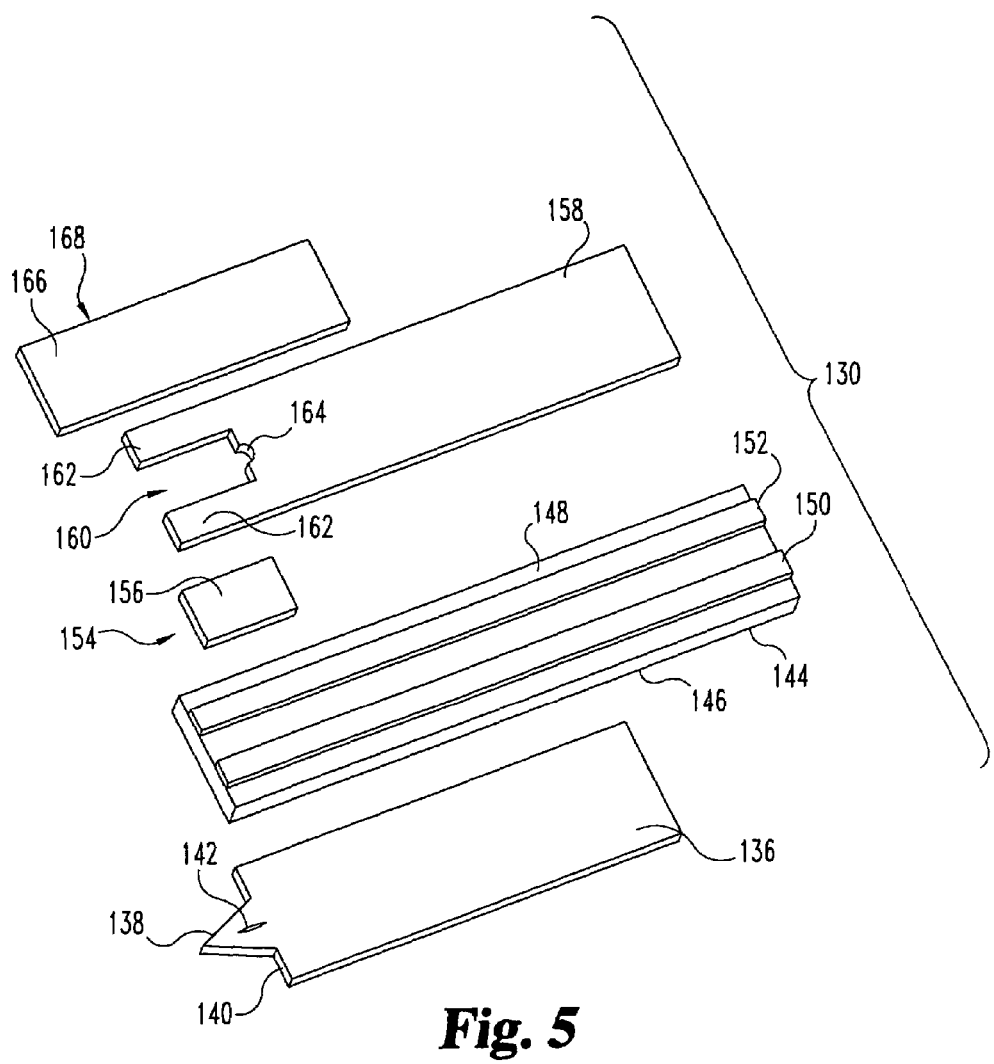
FIG. 5 is an exploded view of the FIG. 4 lancing test strip.

An integrated sampling lancet or device 130 according to another embodiment of the present invention is illustrated in FIGS. 4 and 5. The device 130 in the illustrated embodiment is configured to test the bodily fluid sample through electrochemical analysis. For a detailed discussion of electrochemical analysis of fluid samples, please refer to U.S. Pat. No. 6,270,637 to Crismore et al., which is hereby incorporated by reference in its entirety. Device 130 has many components that are similar to device 60 illustrated in FIGS. 1-3, with the notable exceptions described below. Like the previous embodiment, device 130 is configured to lance an incision into the skin and draw fluid from the incision into a test area via a flexible sheet.

As depicted in FIG. 4, device 130 has a sampling end portion 132 that is configured to collect a fluid sample and a connection end portion 134 that is adapted to connect to a meter. Referring to FIG. 5, device 130 includes an incision forming member or lancet 136 that is used to form an incision in the skin. At the sampling end portion 132, lancet 136 has a lancet tip 138 extending from a depth stop edge 140. Tip 138 defines a capillary slot 142 that is constructed to draw fluid via capillary action into the device 130. In the illustrated embodiment, lancet tip 138 has a generally triangular shape, but it should be appreciated that in other embodiments, tip 138 can be shaped differently. Further, the device 130 in the illustrated embodiment has an overall flat shape so that device 130 can be easily mass-produced by laminating its various components together.

The lancet 136 is attached to an insulating substrate 144, which has a blade surface 146 and an electrode surface 148. As show in FIG. 4, the lancet 136 is attached to blade surface 146 of the substrate 144. In one embodiment, blade 136 is attached to the substrate 144 through an adhesive. It should be appreciated, however, that blade 136 can be attached to substrate 144 in other manners. In one particular form, the blade 136 can be attached to the remainder of device 130 after blade 136 has been sterilized. This eliminates the need to recalibrate the device 130 due to the undesirable effects of sterilization. Substrate 144 may be made of any useful insulating material, such as plastic. By way of a nonlimiting example, the insulating substrate 144 can be made of vinyl polymers, polyamides, polyesters, and styrenics in order to provide the electrical and structural properties that are desired.

On the electrode surface 148, the substrate has first 150 and second 152 conductors attached thereto. In one form, conductors 150 and 152 are attached to the substrate 144 with an adhesive and extend in a parallel relationship with respect to one another. However, it is contemplated that conductors 150 and 152 can be attached in other generally known manners. As shown, conductors 150 and 152 in the illustrated embodiment extend from the connection end 134 to the sampling end 132 of the device 130. The conductors 150 and 152 act as electrodes for analyzing the fluid with the device 130. In one embodiment, conductor 150 acts as an electrically conductive working electrode and conductor 152 acts as a counter or reference electrode. Conductors 150 and 152 can be made from electrically conductive materials such as silver, silver chloride and/or palladium, to name a few. In the illustrated embodiments, conductors 150 and 152 are made of palladium. It is contemplated that device 130 can include three or more electrodes. For example, with a three electrode arrangement, a third conductor is placed between conductors 150 and 152. In this arrangement, the third conductor acts as a reference electrode while conductor 150 acts as a working electrode and conductor 152 acts as a counter electrode. It is further contemplated that in other embodiments the substrate 144 can be optional such that the conductors 150 and 152 can be directly applied to the blade 136, when blade 136 is made from or coated with an insulating material.

At the sampling end portion 132, the device 130 includes a test area 154 in which the fluid is analyzed. The test area 154 includes an electrochemical reagent test strip or coating 156. In the illustrated embodiment, reagent 156 spans between and covers a portion of both conductors 150 and 152. In another embodiment, the reagent 156 only contacts electrodes 150 and 152. It is contemplated that reagent 156 may be applied to the entire exposed area of conductors 150 and 152 or may cover only a portion of the exposed portions of conductors 150 and 152.

In FIG. 4, a spacer 158 overlays the electrodes 150 and 152 as well as the substrate 144. In one embodiment, spacer 158 is glued to the substrate 144, and the spacer 158 is made from an electrically insulative material of the type described above for substrate 144. As should be appreciated, the spacer 158 can be attached to the substrate 144 in other manners. At connection portion 134, conductors 150 and 152 are exposed such that the integrated test strip 130 can be operatively coupled to a bodily fluid sampling meter, such as an ACCU-CHEK® COMPACT™ brand meter or an ACCU-CHEK® ADVANTAGE® brand meter (Roche Diagnostics Corporation, Indianapolis, Ind.).

In the test area 154, the spacer 158 defines a sampling channel or cavity 160 in which the bodily fluid sample is collected. In one embodiment, channel 160 is sized to form a capillary channel for drawing fluid via capillary action. The dimensions of channel 160 can be similar to the dimensions given above for the capillary channel 98 in the device 60 illustrated in FIGS. 1-3. As shown in FIG. 5, channel 160 is defined by a pair of spacer arms 162 that extend from spacer 158. In channel 160, the spacer 158 further defines an air vent notch 164 that is used in venting air from channel 160. A collection member or sheet 166 overlays the sampling channel 160 such that channel 160 is sandwiched between the sheet 166 and the substrate 144. In the illustrated embodiment, collection member 166 is in the form of a flexible sheet. In one particular form, sheet 166 is a transparent plastic film so as to allow the user to visualize the droplet of fluid at the incision and in the channel 160 during sampling. Moreover, sheet 166 provides a visual indicator such that the user can see whether the device 130 is positioned close enough to collect the fluid. As should be appreciated, in other embodiment, the sheet 166 can be semi-transparent and/or opaque. As shown, channel 160 opens at the sampling end of device 130. As shown in FIG. 4, an extension portion 168 of sheet 166 as well as lancet tip 138 extend from device 130 at end 132. In one embodiment, portion 168 has the same length as tip 138. In another embodiment, portion 168 of sheet 166 is longer than tip 138 such that sheet 166 can contact the skin when the lancet tip 138 is withdrawn from the skin. It is further contemplated that portion 168 of sheet 166 can be shorter than the lancet tip 138 in other embodiments.

Like the embodiment described above, the fluid flow in the device 130 of FIGS. 4-5 may be enhanced by forming the channel 160 and/or the sheet 166 from a material which is hydrophilic, which has been treated to be hydrophilic, or which has been coated with a hydrophilic material such as a surfactant or hydrophilic polymers. The surfaces can also be treated using polyamides, oxidation (e.g. corona/plasma treatment); plasma chemical vapor deposition; vacuum vapor deposition of metals, metaloxides or non-metaloxides; or deposition of an element which oxidizes with water. In one form, the entire sheet 166 and channel 160 are coated with a layer of aluminum oxide in order to enhance wicking of fluid into the channel 160 and promote fluid flow in channel 160.

Figure 6:
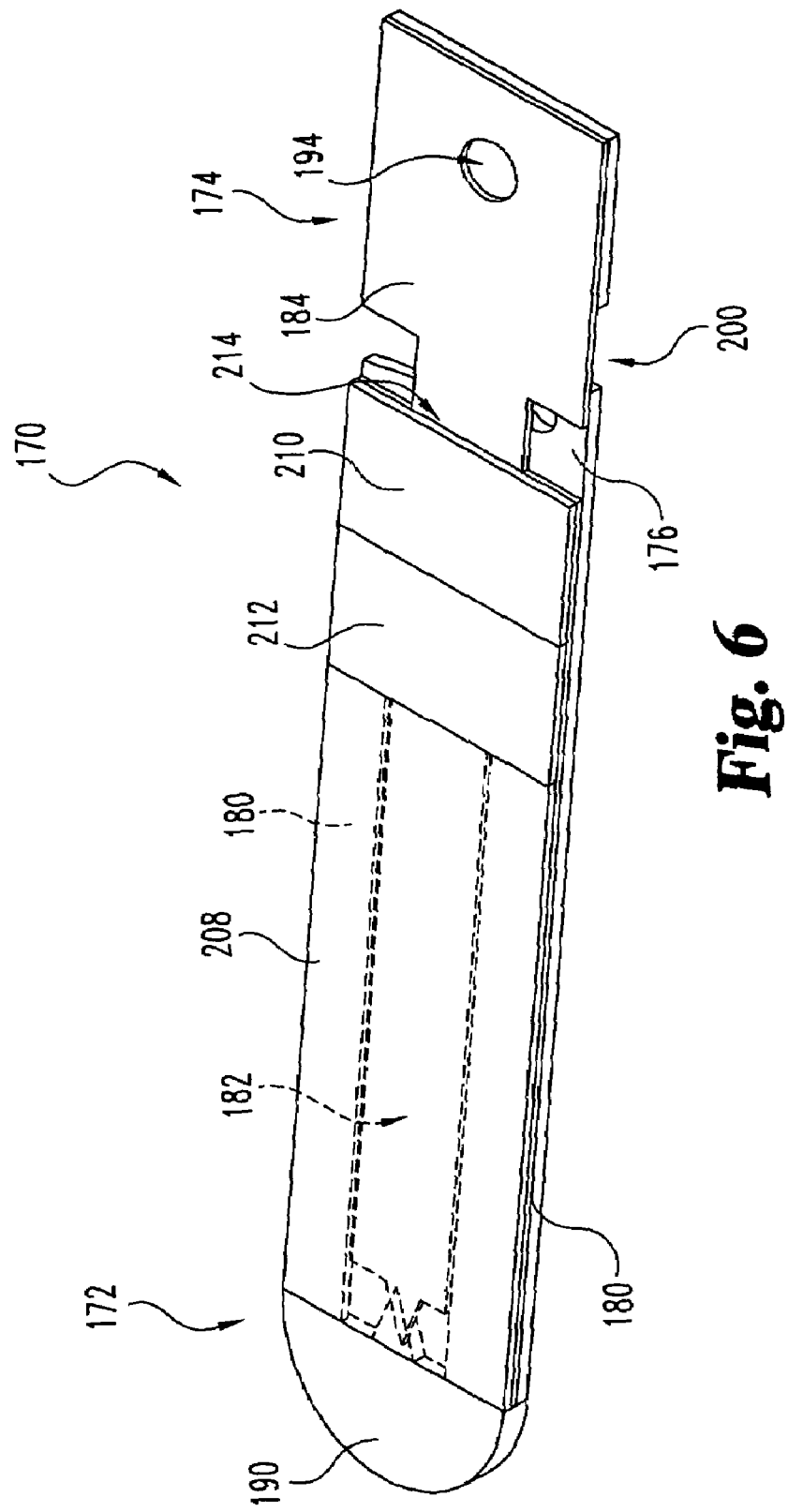
FIG. 6 is a perspective view of an integrated lancing test strip according to another embodiment of the present invention.
Figure 7:
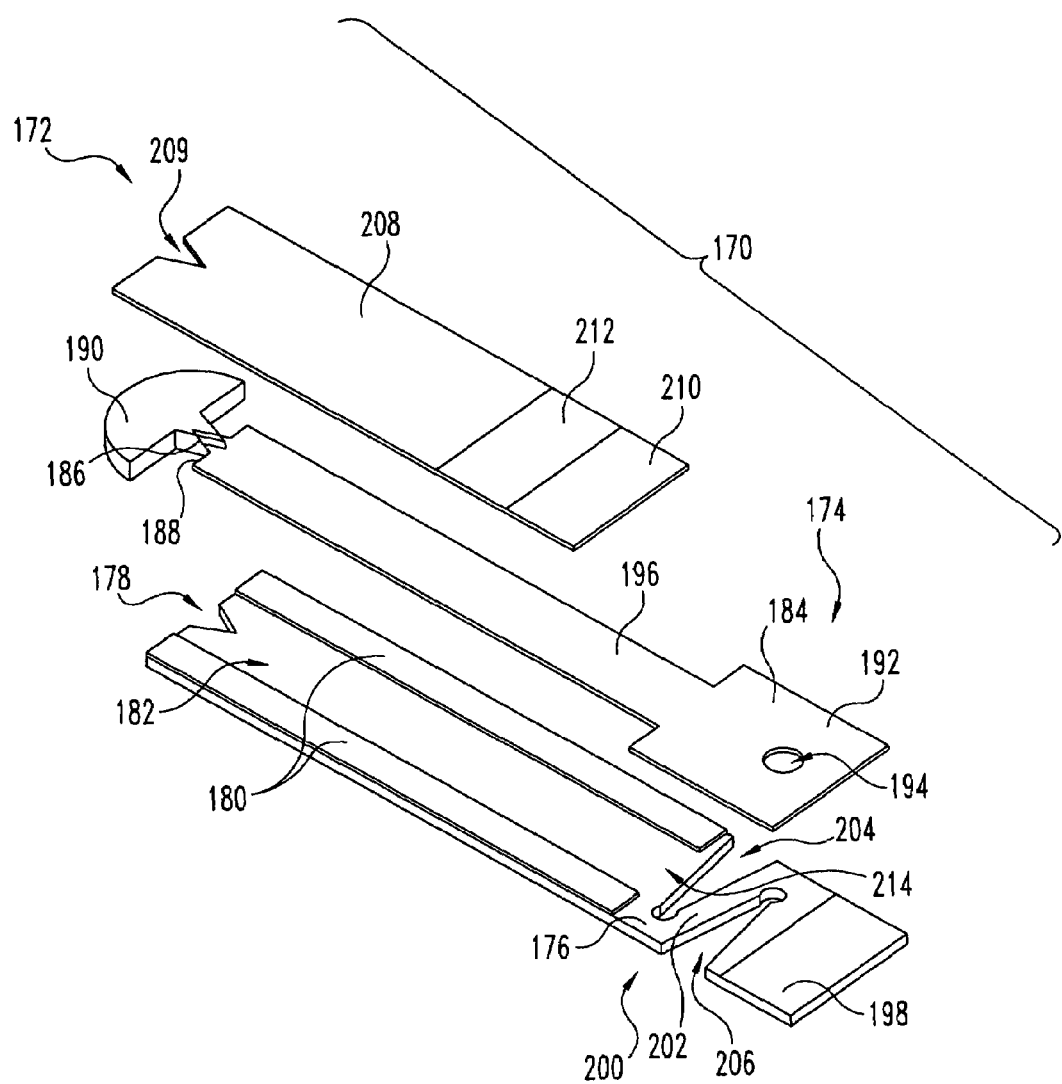
FIG. 7 is an exploded view of the FIG. 6 lancet.

As mentioned above, the assembled test strip 130 can be used in conjunction with a meter capable of measuring analyte levels of the fluid sample through electrodes 150 and 152. During lancing, sheet 166 bends such that tip 138 is able to form an incision in the skin. As the tip 138 is withdrawn from the incision, a droplet of bodily fluid collects on the surface of the skin. The sheet 166 is positioned either to contact the skin or positioned proximal to the skin such that fluid is wicked up the sheet 166 and into channel 160 via capillary action. Once a sufficient amount of fluid is collected, the fluid sample can be analyzed in test area 154 using a number of known techniques. For instance, electrical current through reagent 156 between conductors 150 and 152 can be used to analyze the fluid. It should be understood that other electrical properties may be measured, such as voltage, resistance and/or impedance in order to analyze the fluid. Referring to FIGS. 6 and 7, an integrated sampling device 170 according to another embodiment has a sampling end portion 172 and an actuation end portion 174. Similar to the previously described embodiments, device 170 has a capillary channel for drawing a fluid sample onto a test strip in the device. However, in this embodiment, the lancet for forming an incision in the skin is slidably received in the capillary channel. As shown, device 170 in FIGS. 6-7 has a generally flat shape, which makes mass production of device 170 simpler. At the sampling end portion 172, base 176 defines a notch 178 in order to reduce dose hesitation and promote collection of bodily fluid. In one embodiment base 176 is formed from a metallic foil, and the notch 178 is v-shaped. Base 176 in another embodiment is formed from plastic. In one particular form, base 176 is formed from a melonex type foil. As should be appreciated, other types of materials may be used to form base 176.

A pair of spacer members 180, which define a capillary channel 182, are attached to base 176. In one embodiment, spacer member 180 are formed from beads of adhesive, and in other embodiment, spacer members 180 are formed from adhesive tape. It should be appreciated that spacer members 180 can be formed from other types of materials. In one form, channel 182 is coated with a hydrophilic material in order to enhance fluid flow in the channel 182. Device 170 further includes a lancet or blade member 184 that is slidably received in channel 182. In one form, the lancet 184 is made from stainless steel, but it is contemplated that lancet 182 can be made from other materials. As shown, the lancet 184 in this embodiment is substantially flat. Prior flat lancets needed to be thick in order to be rigid enough to resist lateral deflection during lancing. Device 170 allows the flat lancet 184 to formed from thinner material than previously possible, which in turn may reduce may reduce the pain associated with lancing. By being positioned inside the channel 182, the lancet is supported and stabilized by the device 170 throughout most of its length so that the lancet remains in proper alignment during lancing. The support provided by the device 170 around the lancet 184 prevents the lancet 184 from laterally deflecting or bending during lancing, which in turn prevents the incision from being formed at the wrong location or angle. Moreover, this configuration ensures that the capillary channel 182 is positioned directly over the incision.

At the sampling end portion 172, lancet 184 has a lancet tip 186 that extends from stop edge 188. In the illustrated embodiment, the lancet tip 186 has a generally triangular shape, but it should be appreciated that the lancet tip 186 can have a different shape. Device 170 further includes a protective tip cover 190 that protects the user from accidentally cutting themselves with the lancet tip 186 and further preserves the sterility of the lancet tip 186. At the actuation end portion of device 170, lancet 184 includes a head portion 192 that defines a registration opening 194. The registration opening 194 is used for securing and positioning device 170 in a meter. Between tip 186 and head 192, a body portion 196 of the lancet 184, which is narrower than the head portion 192, is slidably received in channel 182. In one embodiment, the head portion 192 of lancet 184 is secured to the actuation end portion 174 of the base 176 through an adhesive 198. Nevertheless, it should be appreciated that lancet 184 can be secured to base 176 in other manners.

Normally, lancet tip 186 is retracted inside capillary channel 182. However, during lancing, the lancet tip 186 extends from the sampling end portion 172 of the device 170. In order to retract and maintain the tip 186 inside channel 182, the device 170 includes a retraction mechanism 200. In the illustrated embodiment, the retraction mechanism 200 includes a spring arm 202 that is formed by a pair of opposing spring notches 204 and 206 defined in the base 176. In order to control the penetration depth of the lancet tip 186, movement of the head portion 192 during lancing is stop by the spacer members 180.

As depicted in FIG. 7, device 170 further incorporates a cover 208 that encloses the capillary channel 182. The cover 208 is secured to spacers 180, and the cover 208 defines a notch 209 for reducing dose hesitation. In one embodiment, the cover 208 is formed from a melonex type foil. It is contemplated that cover 208 can be formed from other types of materials. Device 170 further has a vent member 210 attached to the spacers 180. As shown in FIG. 6, a test strip or media 212 is attached to the spacers 180 between the cover 208 and the vent member 210. The vent member 210 defines a vent opening 214 through which air or some other gas from channel 218 can be exhausted to enhance the fluid flow in channel 182. The test strip 212 can be of the type described above, such that it is able to test analyte levels in fluid via electrical, electrochemical, magnetic and/or optical techniques, to name a few. In one embodiment, the test strip is a chemical reagent test strip. It is further contemplated that device 170 can incorporate the collection sheets 76, 166 of the type described above with reference to FIGS. 1-5 in order to promote wicking of the bodily fluid sample into the capillary channel 182.

During testing, the sampling end portion 172 of the device is pressed against the skin, and the lancet tip 186 is extended from the device 170 in order to cut an incision in the skin. Tip 186 of the lancet 184 can be manually extended by the user or automatically extended, through a hammer or other means for example. After the incision is formed, the retraction mechanism 202 retracts the tip 186 back into the device 170. Next, the sampling end portion 172 of device 170 either remains in contact with the skin or is positioned proximal to the droplet of blood such that notches 178 and 209 draw the bodily fluid from the droplet into the capillary channel 182 around the lancet 184. In capillary channel 182, the fluid around the lancet 184 is drawn via capillary action onto the test strip 212. Once deposited on the test strip 212, the fluid can be analyzed using the bodily fluid analysis techniques described above.

Figure 10:
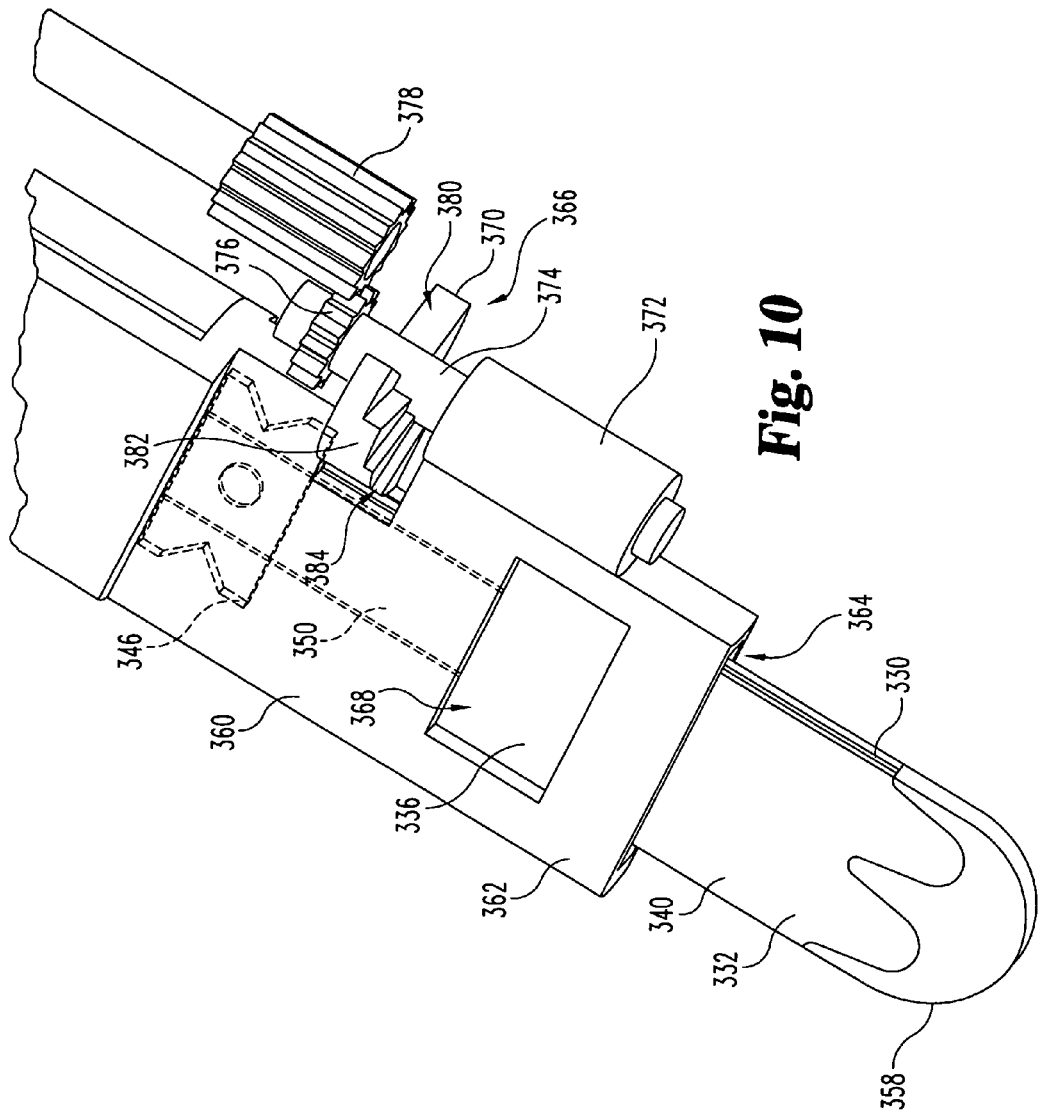
FIG. 10 is a perspective view of the FIG. 8 lancet mounted in a sampling device.

FIGS. 8-10 illustrate a sampling device 330 according to another embodiment of the present invention. As will be appreciated from the discussion below, device 330 has a number of features that are common with the embodiments described above, with the notable exceptions discussed below. As shown in FIGS. 8 and 9, device 330 includes a housing 332, an incision forming member or lancet blade 334 slidably received in the housing 332, and test media 336 for analyzing the fluid sample. The blade 334 extends from the housing 332 in order to form an incision in the skin, and fluid from the incision, which is drawn inside the housing 332 around the blade 334, is deposited onto the test media 336 for analysis. Similar to the previous embodiments, device 300 incorporates vent member 337 that defines a vent opening between the test media 336 and the vent member 337 for enhancing fluid flow. Housing 332 has a base 338 and a cover 340 that are attached together through a pair of spacers 342 in order to form a blade cavity 344 in which blade 334 is received. In the illustrated embodiment, both the base 338 and the cover 340 are generally flat to give the sampling device 330 an overall flat appearance. In one form, spacers 342 are beads of adhesive that adhere the base 338 and the cover 340 together. However, it should be understood that spacers 342 can be formed from other types of materials. Conceptually, the housing 332 can be further subdivided into separate head 346 and sampling 348 end portions. Blade 334 is attached to the head 346 and is slidable within blade cavity 344 in the sampling portion 348 of the housing 332. In one embodiment, blade cavity 344 is sized to draw fluid into the housing 330 via capillary action.

Like the device 170 illustrated in FIGS. 6-7, integrated lancet device 330 incorporates a retraction mechanism 349 that retracts the blade 334 inside the housing 332 after lancing. In the illustrated embodiment, the retraction mechanism 349 includes a leaf spring 350 defined in base 338 that connects the head 346 to the sampling portion 348 of the housing 332. The head 346 can further have notches 352 for securing device 330 to a holder. FIGS. 8 and 9 illustrate the leaf spring 350 in a flexed state when blade 334 is extended from the housing 332 through opening 353. Next to opening 353, the base 338 of the housing 332 has a skin contacting edge 354 that acts as a reference surface for controlling the penetration depth of the blade 334 during lancing. Opposite edge 354, the cover 340 has a capillary notch 356 for drawing fluid via capillary action into the blade cavity 344. As shown, the capillary notch 356 in the illustrated embodiment has a gradual tapered shaped from opening 353 to improve fluid flow from the incision into the blade cavity 344 by reducing dose hesitation. As shown in FIG. 10, capillary notch 356 as well as opening 353 can be covered with a safety cover 358 that can be used to maintain the sterility of blade 334 and to protect the user from injury.

In the blade cavity 344, especially between the blade 334 and the cover 340, a gap 359 is formed around the blade 334 for drawing bodily fluid from the incision to the test media 336 via capillary action. The test media 336 can be of the type described above and can be attached to the housing 332 along cavity 334 in a number of manners. For instance, the test media 336 can be a chemically reactive reagent strip that is glued to the housing. To ensure proper calibration of the test media 336, the test media 336 can be attached to the housing 332 after the blade 334 has been sterilized. Once attached, the test media 334 defines portion of the blade cavity 344 and fluid from slot 356 can be drawn to the test media 332 through the blade cavity 334. As mentioned above, vent member 337 defines a vent opening along cavity 334 for exhausting air or some other gas out of the blade cavity 334. It is further contemplated that device 330 can incorporate the collection sheets 76, 166 of the type described above with reference to FIGS. 1-5 in order to promote wicking of the bodily fluid sample into the blade cavity 344.

A holder 360 for device 330 that is operable to adjust the penetration depth of the blade 334 is illustrated in FIG. 10. In the illustrated embodiment, holder 360 is incorporated into a fluid sampling meter. Holder 360 has an enclosure 362 with a receptacle 364 in which device 330 is received and a depth control mechanism 366 that is coupled to the enclosure 362. In the illustrated embodiment, a test media view window 368 is defined in the enclosure 362 such that the test media 336 is able to be viewed for analysis. For instance, window 368 can allow the test media 336 to be analyzed optically. However, it should be appreciated that window 368 can also permit other types of analysis and techniques, such as electrochemical analysis. The depth control mechanism 366 has a depth adjustment wheel 370 that is rotatably coupled to a bearing member 372 through rod 374. As shown, the bearing member 372 is attached to the enclosure 362. The rod 374 has a gear 376 that is engageable with an actuation gear 378. Wheel 380 only partially extends around rod 374, thereby defining a gap 380 that allows device 330 to be mounted in the holder 360. As shown, the wheel 380 has a series of steps 382 of graduated thicknesses, and the steps 382 of wheel 380 can be rotated through a slot 384 in the cover 362.

To insert device 330 into holder 360, the actuation gear 378 rotates the wheel 380 such that gap 380 is positioned over the slot 384. Device 330 is then slid into the receptacle 364 SO that the head 346 of the device 330 is slid past slot 384. Next, the actuation gear 378 rotates the wheel 380 such that at least one of the steps 382 is positioned in the slot 384 between the head 346 and the sampling portion 348 of device 330, thereby securing the device 330 to the holder 360. The step 382 with the appropriate thickness can be positioned in the slot 384 between the head 346 and the skin contacting portion 348 so as to control the penetration depth of the blade 334. During lancing, as the holder 360 is driven towards the skin, the skin contacting edge 354 contacts the surface of the skin and flattens the skin around the incision site, thereby providing a suitable surface from which to gage the penetration depth of the blade 334. As the holder 360 is driven further, the skin contacting portion 348 of the housing 332 slides within the receptacle 364 towards the head 346 of the device 330 such that the blade 334 is uncovered to lance the skin. The skin contacting portion 348 of the housing 332 continues to retract until it engages the selected step 382 on the wheel 380. As previously mentioned, the thickness of the step 382 controls the penetration depth of the blade 334. After the incision is formed, the leaf spring 350, which became flexed during lancing, extends portion 348 of the housing 332 so as to recover the blade 334. As the bodily fluid from the incision forms a drop on the skin, opening 353 of device 330 is positioned proximal the incision in the skin. In one embodiment, the skin contacting edge 354 of device 330 remains in contact with the skin as the drop of fluid forms. In another embodiment, the skin contacting edge 354 is positioned proximal the skin to collect the drop of fluid. The fluid is then drawn via capillary action inside the blade cavity 344. Next, the fluid travels through the blade cavity 344 and is deposited on the test media 336 for analysis.

Figure 11:
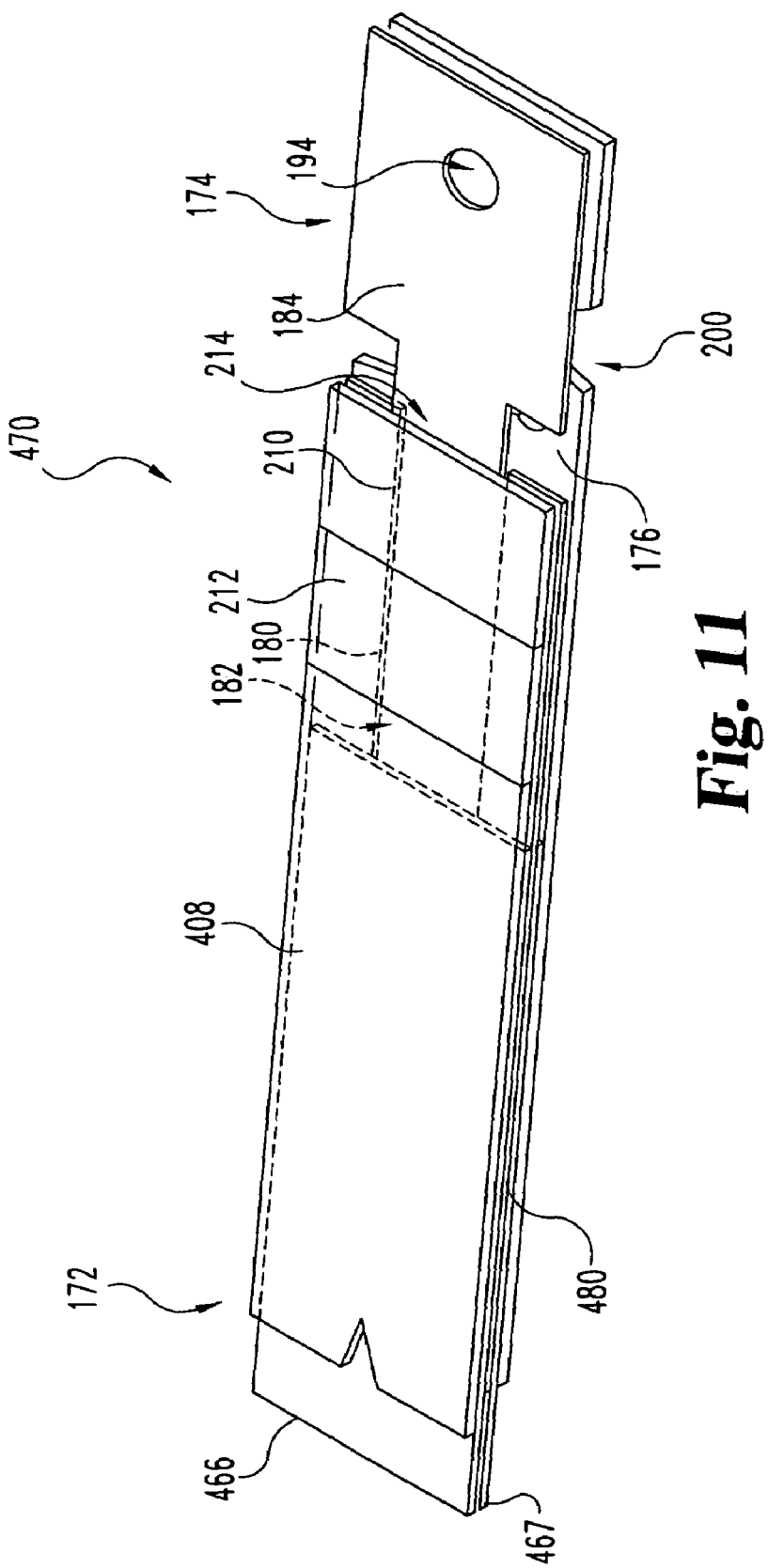
FIG. 11 is a perspective view of an integrated lancing test strip according to another embodiment of the present invention.
Figure 12:
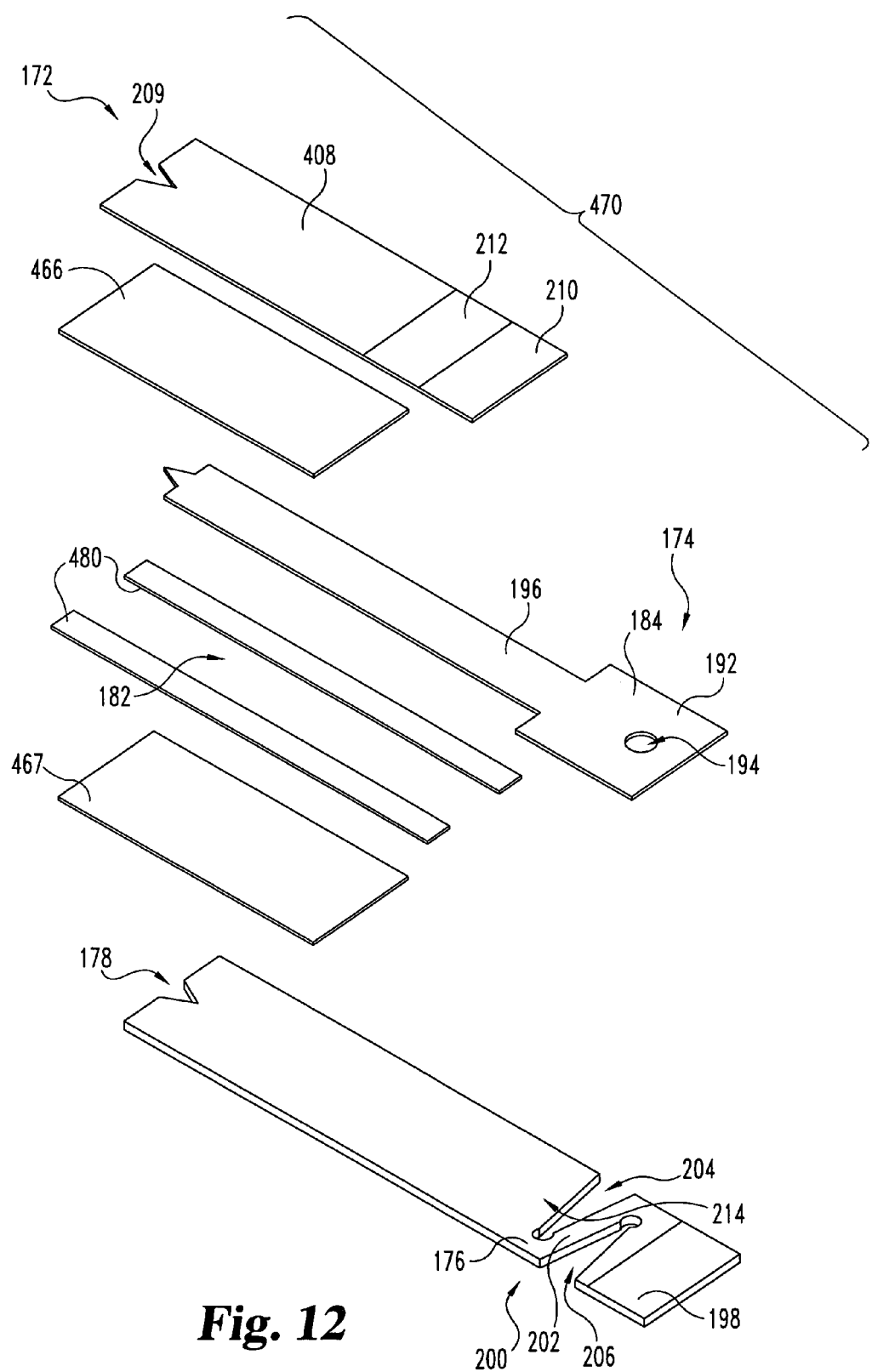
FIG. 12 is an exploded view of the FIG. 11 lancet.

Referring to FIGS. 11 and 12, an integrated sampling device 470 according to another embodiment is a variation of the embodiment of device 170 shown in FIGS. 6-7. Similar to previously described embodiments device 470 has a capillary channel 182 for drawing a fluid sample. Device 470 additionally incorporates a cover 408 that extends beyond base 176 at the sampling end portion 172. This arrangement allows the sampling end portion 172 to be pushed into the skin surrounding an incision with no ill effect. The uneven lengths of the cover 408 and base 176 create a bevel that applies the pushing force into the skin asymmetrically around the incision tending to keep the incision open. Alternatively, base 176 could extend beyond cover 408 to achieve the same benefit.

Device 470 additionally incorporates collection sheets 466 and 467 on opposite sides of a pair of spacer members 480. Sheet 466 is positioned between the cover 408 and the spacer members 480. Sheet 467 is positioned between the spacer members 480 and the base 176. The pair of spacer members 480 and collection sheets 466 and 467 define a capillary channel 182. Device 470 further includes a lancet 184 that is slidably received in channel 182.

Collection sheets 466 and 467 have the same properties and characteristics previously described collection members or sheets 76 and 166. As shown in FIGS. 11 and 12, sheets 466 and 467 face each other and are separated by spacer members 480. Collection sheets 466 and 467 extend beyond cover 408 and base 176 to facilitate drawing body fluid into the capillary channel 182 without closing the incision. By incorporating multiple collection sheets 466 and 467, device 470 collects fluid over a larger area without having to be moved. It is further contemplated that device 470 incorporates only a single sheet, either sheet 466 or sheet 467. It is further contemplated that sheets 466 and 467 have the same or shorter length as base cover 408 and base 176.

Device 470 operates similarly to the previously described operation of device 170. The differences in operation arise after the incision is formed. An incision is formed as previously described with device 170. After the incision is formed, the sampling end portion 172 of device 470 remains in contact with the skin or is positioned above the fluid such that collection sheets 466 and 467 are in contact with the fluid. Collection sheets 466 and 467 draw the fluid from the incision into the capillary channel 182. The bodily fluid may be collected in the capillary channel 182. Alternatively, the bodily fluid may be drawn by capillary action onto the test strip 212. Once deposited on the test strip 212, the fluid can be analyzed using the bodily fluid techniques described above.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A device for sampling a bodily fluid from an incision in skin, comprising:

a lancet having a lancet tip to form the incision in the skin;

a housing coupled to the lancet, the housing defining at least in part a capillary channel with an opening, the capillary channel being sized to draw the bodily fluid from the incision via capillary action;

the lancet tip extending from the capillary channel opening, the lancet tip being immovable relative to the housing;

a flexible sheet having a sampling end portion extending from the opening of the capillary channel;

the sampling end portion being flexible to bend against the skin as the lancet forms the incision; and the sampling end portion of the flexible sheet being at least as long as the lancet tip to draw the bodily fluid into the opening of the capillary channel when the lancet tip is retracted from the incision.

2. The device of claim 1, wherein the housing defines a notch at the opening of the capillary channel to minimize dose hesitation of the bodily fluid into the capillary channel.

3. The device of claim 1, wherein the sheet is hydrophilic for enhancing the flow rate of the bodily fluid into the capillary channel.

4. The device of claim 3, wherein the sheet is coated with a hydrophilic coating.

5. The device of claim 4, wherein the hydrophilic coating includes aluminum oxide.

6. The device of claim 1, wherein the sheet is transparent for allowing a user to view the bodily fluid while being drawn into the capillary channel.

7. The device of claim 1, wherein:
the housing has an outside surface; and
the lancet is attached to the outside surface of the housing.

8. The device of claim 7, wherein the lancet is glued to the outside surface of the housing.

9. The device of claim 1, wherein the housing defines a registration opening for positioning the housing.

10. The device of claim 1, wherein:
the housing includes a base and a spacer member attached to the base;
the spacer member defines a slot;
the sheet covers at least a portion of the slot; and
the spacer member is sandwiched between the base and the sheet to form the capillary channel in the slot.

11. The device of claim 10, wherein the housing includes a cover covering the sheet over the slot and a vent member defining a vent opening for exhausting gas from the capillary channel.

12. The device of claim 11, further comprising a test area positioned along the capillary channel in which the bodily fluid is analyzed, wherein the vent opening is defined between the test area and the vent member.

13. The device of claim 12, wherein the test area includes a reagent test strip.

14. The device of claim 10, further comprising a test area positioned along the capillary channel for analyzing the bodily fluid.

15. The device of claim 1, wherein the lancet tip has a triangular shape.

16. The device of claim 1, wherein the lancet tip has a slanted shape.

17. The device of claim 1, wherein the lancet tip defines a slot for drawing the bodily fluid into the capillary channel.

18. The device of claim 1, wherein the sheet extends past the lancet tip in order for the sheet to remain in contact with the skin and draw the bodily fluid when the lancet tip is removed from the skin.

19. The device of claim 1, wherein the housing and the lancet are flat.

20. The device of claim 1, further comprising means for testing the bodily fluid in the capillary channel.

21. The device of claim 20, wherein the means for testing the bodily fluid includes a reagent test strip.

22. The device of claim 1, further comprising a testing system positioned along the capillary channel to analyze the bodily fluid.

23. The device of claim 22, wherein the testing system includes a reagent test strip.

24. The device of claim 22, wherein the testing system includes:

at least two electrodes; and
an electrochemical test strip positioned between the electrodes in the capillary channel.

25. The device of claim 24, wherein the housing includes:
a base made of insulating material, the electrodes extending along the base; and
a spacer made of insulating material, the electrodes being sandwiched between the base and spacer, the spacer defining a slot, wherein said sheet covers the slot to form the capillary channel.

26. The device of claim 22, wherein:
the sheet is hydrophilic; and
the sheet extends along the capillary channel to draw the bodily fluid onto the test system.

27. The device of claim 1, wherein the housing has a skin contact surface that is shaped to maintain the incision open as the housing is pressed against the skin.

28. The device of claim 27, wherein the skin contact surface and the housing are beveled.

29. The device of claim 1, further comprising a second flexible sheet extending from the housing on the opposite side of the capillary channel as the flexible sheet to draw the bodily fluid into the opening of the capillary channel without closing the incision.

30. The device of claim 29, wherein the flexible sheet and the second flexible sheet face each other.

31. The device of claim 1, wherein the lancet tip and the sampling end portion of the flexible sheet extend in a generally parallel manner.

32. The device of claim 1, wherein the flexible sheet is a plastic film.

33. A method of sampling a bodily fluid from an incision in skin, comprising:
providing a device that includes a housing that defines a capillary channel with an opening, a lancet coupled to the housing, and a flexible sheet that extends from the opening of the capillary channel, wherein the lancet includes a lancet tip extending from the opening of the capillary channel;
lancing the incision in the skin with the lancet;
bending the flexible sheet against the skin during said lancing;
retracting the lancet from the skin;
straightening the flexible sheet during said retracting; and
drawing the bodily fluid from the incision into the capillary channel with the flexible sheet.

34. The method of claim 33, further comprising:
wherein the device includes testing means positioned along the capillary channel;
depositing the bodily fluid in the capillary channel onto the testing means; and
analyzing the bodily fluid with the testing means.

35. The method of claim 34, wherein said analyzing includes chemically testing analyte levels in the bodily fluid.

36. The method of claim 34, wherein said analyzing includes electrochemically testing analyte level in the bodily fluid.

37. The method of claim 33, further comprising:
wherein the device includes testing means positioned along the capillary channel;
depositing the bodily fluid in the capillary channel onto the testing means; and
analyzing the bodily fluid with the testing means.

38. An integrated bodily fluid sampling device for sampling a bodily fluid from an incision in skin, comprising:
a housing defining a capillary channel with an opening configured to draw the bodily fluid via capillary action;

a lancet having a lancet tip for forming the incision in the skin, the lancet being attached to the housing with the lancet tip extending from around the opening of the channel, the lancet being immovable with respect to the housing;

means for testing the bodily fluid positioned along the channel;

a sheet of hydrophilic film extending from the opening of the channel, the sheet being flexible to bend as the lancet tip forms the incision; and the sheet extending past the lancet tip for drawing the bodily fluid into the channel.

39. The device of claim 38, wherein the means for testing the bodily fluid includes a chemical reagent test strip.

40. The device of claim 38, wherein the means for testing the bodily fluid includes at least a pair of electrodes and an electrochemical reagent spanning between the electrodes.

41. The device of claim 38, wherein the lancet has a flat shape.

42. The device of claim 38, wherein the housing includes:
a base;
a cover; and
a spacer sandwiched between the base and the cover to define the channel.

43. The device of claim 42, wherein the lancet, the base, the cover and the lancet have an overall flat shape.

44. The device of claim 38, wherein the housing defines a notch at the opening of the channel for minimizing dose hesitation of the bodily fluid into the opening.

45. An apparatus, comprising:
a body fluid sampling device including
a lancet having a lancet tip for cutting an incision in skin,
a capillary channel opening for collecting body fluid from the incision,
the lancet tip extending in a fixed manner from the capillary channel opening,
a fluid collection sheet having a sampling end portion extending from the capillary channel opening, and
the sampling end portion of the fluid collection sheet being at least as long as the lancet tip for drawing the body fluid from the incision into the capillary channel opening.

46. The apparatus of claim 45, in which the sampling end portion extends past the lancet tip.

47. A method, comprising:
cutting an incision in skin with a lancet of a body fluid sampling device that includes a capillary channel with an opening, wherein the lancet is immovable relative to the body fluid sampling device, wherein the sampling device includes a fluid collection sheet that is flexible;
bending the fluid collection sheet against the skin during said cutting the incision;
retracting the lancet from the incision; and
drawing body fluid from the incision into the opening of the capillary channel with the fluid collection sheet.

48. The method of claim 47, further comprising:
wherein the fluid collection sheet extends past the end of the lancet; and
maintaining contact of the fluid collection sheet against the skin during said drawing the body fluid.

* * * * *